(12) United States Patent
Giuliani et al.

(10) Patent No.: US 9,394,335 B2
(45) Date of Patent: Jul. 19, 2016

(54) ESTERS OF GLYCYRRHETINIC ACID, PREPARATION AND COSMETIC APPLICATIONS THEREOF

(71) Applicant: GIULIANI S.P.A., Milan (IT)

(72) Inventors: Giammaria Giuliani, Milan (IT); Anna Benedusi, Milan (IT); Guido Bregaglio, Gubbio (IT); Antonio Mascolo, Milan (IT)

(73) Assignee: GIULIANI S.P.A., Milan (IT)

( * ) Notice: Subject to any disclaimer, the term of this patent is extended or adjusted under 35 U.S.C. 154(b) by 0 days.

(21) Appl. No.: 14/653,091

(22) PCT Filed: Dec. 18, 2013

(86) PCT No.: PCT/IB2013/061087
§ 371 (c)(1),
(2) Date: Jun. 17, 2015

(87) PCT Pub. No.: WO2014/097176
PCT Pub. Date: Jun. 26, 2014

(65) Prior Publication Data
US 2015/0337005 A1    Nov. 26, 2015

(30) Foreign Application Priority Data

Dec. 18, 2012 (IT) .................. MI2012A2169

(51) Int. Cl.
*C07J 63/00* (2006.01)
*A61Q 19/00* (2006.01)
*A61Q 19/08* (2006.01)
*A61K 8/63* (2006.01)
*A61Q 1/14* (2006.01)
*A61Q 5/02* (2006.01)

(52) U.S. Cl.
CPC ............... *C07J 63/008* (2013.01); *A61K 8/63* (2013.01); *A61Q 19/00* (2013.01); *A61Q 19/08* (2013.01); *A61Q 1/14* (2013.01); *A61Q 5/02* (2013.01); *A61Q 19/005* (2013.01)

(58) Field of Classification Search
None
See application file for complete search history.

(56) References Cited

FOREIGN PATENT DOCUMENTS

| EP | 1468696 | 10/2004 |
| WO | 2009115455 | 9/2009 |

OTHER PUBLICATIONS

Database Caplus Chemical Abstracts Service, Columbus, Ohio, US; Database Accession No. 2009:176720, Abstract of US 20090042846, Gupta, Bioderm Research, USA, Feb. 12, 2009.*
International Search Report dated Feb. 28, 2014 corresponding to PCT/IB2013/061087 4 pages.
Written Opinion dated Feb. 28, 2014 corresponding to PCT/IB2013/061087 4 pages.
International Preliminary Report on Patentability dated Jul. 1, 2015 corresponding to PCT/IB2013/061087 6 pages.

* cited by examiner

*Primary Examiner* — Karl J Puttlitz
(74) *Attorney, Agent, or Firm* — Ohlandt, Greeley, Ruggiero & Perle, L.L.P.

(57) ABSTRACT

An ester of glycyrrhetinic acid with (poly)glycerol-sorbitol and cosmetic compositions thereof is described. The introduction of sorbitol in the (poly)glycerol chain determines an increase in solubility of the ester of the invention increasing solubility in water and the possibility of using glycyrrhetinic acid in cosmetic applications.

10 Claims, 7 Drawing Sheets

ESTERS OF GLYCYRRHETINIC ACID, PREPARATION AND COSMETIC APPLICATIONS THEREOF

TECHNICAL FIELD

The present invention relates to esters of glycyrrhetinic acid with polyglycerol-sorbitol and their applications in the cosmetic field.

STATE OF THE ART

The process of skin ageing consists in the natural evolution of structure and tissues affecting this organ which takes place since the embryonic period and continues until an old age.

Features of skin ageing are a reduction in turnover and cell functions which is followed by a decrease in structural substances (collagen, elastin, etc.) providing tone and elasticity to the skin which per se represents a physical barrier that our body sets against the outer environment. For this reason, its integrity and functionality are a prerequisite to a good health condition of same.

Environmental insults such as ultraviolet rays, exposure to cigarette smoke and polluting substances together with the natural ageing process contribute to the formation of a greater amount of reactive oxygen species (ROS) and free radicals which, when in excess, may shortly lead the body to a condition which negatively affects the integrity of cell proteins, membranes, genes and which is described as oxidative stress.

This stress condition, if prolonged in time, produces a systemic inflammation which in turn determines the known phenomena of cell degeneration strictly correlated to ageing, a process which is therefore connected to the decrease in the protective capabilities of the body (antioxidant defences, DNA repairing processes, etc.). The use of substances with anti-inflammatory or lenitive properties therefore represents an effective strategy to counteract and prevent the onset of this stress condition.

The derivatives of liquorice root (*Glycyrrhiza glabra*) have long been used as lenitive substances in preparation for skin use and there are various conditions for which the topical application of these substances is advantageous, an example being the treatment of eczema, allergic and contact dermatitis and the treatment of psoriasis.

In liquorice root there is a very large number of substances (e.g. salts of glycyrrhizic acid, asparagine, glabridin, glycyrrhetol, formononetin, etc.) which by virtue of their properties may carry out a beneficial action for the skin. Among these substances the most representative from the quantitative point of view are the salts of glycyrrhizic acid.

18-Beta glycyrrhetinic acid is a pentacyclic triterpenoid which is obtained by hydrolysing glycyrrhizic acid, triterpenic saponin, naturally present in the root and rhizome of *Glychyrrhiza Glabra*.

18-Beta glycyrrhetinic acid (glycyrrhetinic acid) originating from the hydrolysis of glycyrrhizic acid is a part of the molecule having lenitive activity:

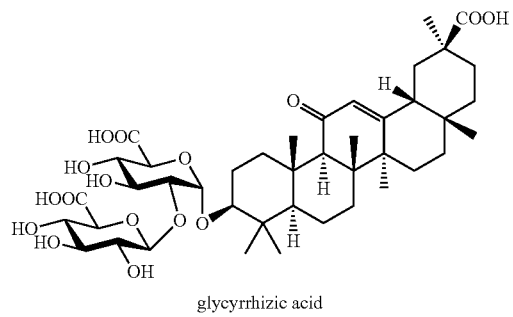

glycyrrhizic acid

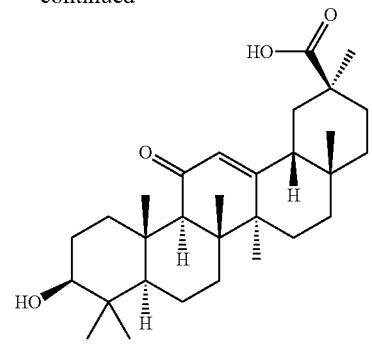

18-beta glycyrrhetinic acid

From the chemical-physical point of view, 18-beta glycyrrhetinic acid is in the form of a white, odourless powder, insoluble in water and oils, while it is soluble in ethanol.

It is known that the introduction of a substance in a formulation may be carried out by different methods firstly depending on the chemical-physical features of the active ingredient and carrier (or formulation) and which accordingly determine their partition or passage of the first one through the various layers making up the skin, up to the possibility of reaching the circulatory system and thus the different tissues of the body.

The latter case is referred to as percutaneous absorption which from the quantitative point of view may be defined as the amount of a certain substance that may be found at a systemic level within a certain time interval after application onto the skin.

In topical administration the active ingredient vice versa has to obtaining the highest local effectiveness with the lowest systemic absorption.

Molecules having a high molecular weight generally are not capable of penetrating into the deepest layers. If not susceptible to hydrolysis, their are bound to remain on the surface.

Therefore there is a need for a product capable of increasing the lenitive effectiveness of glycyrrhetinic acid allowing a modulated passage through the transdermal pathway and the achievement of the deepest layers of derma, and at the same time being highly biocompatible and tolerable by the body.

SUMMARY OF THE INVENTION

The inventors have found that by conveniently modifying an ester of glycyrrhetinic acid it is possible to increase the solubility of glycyrrhetinic acid increasing the possibilities of use of this substance in the cosmetic field.

According to a first aspect the present invention provides an ester of glycyrrhetinic acid having formula (I):

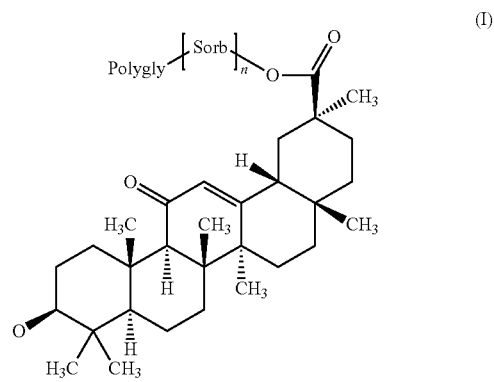

(I)

where n is an integer from 1 to 3,

Sorb represents a moiety of sorbitol, and

Polygly represents a moiety of glycerol or polyglycerol.

According to another aspect, the present invention is directed to a cosmetic composition comprising at least one ester of glycyrrhetinic acid having formula (I) and at least a cosmetically acceptable carrier.

According to a further aspect, the present invention relates to the process for manufacturing such ester of glycyrrhetinic acid having formula (I).

According to an even further aspect, the present invention relates to the use of said ester of glycyrrhetinic acid having formula (I) or of said cosmetic composition as an anti-ageing agent in the topical treatment of the skin, particularly sensitive skin.

BRIEF DESCRIPTION OF THE DRAWINGS

The features and advantages of the present invention will become apparent from the following detailed description and the exemplary embodiments provided by way of non-limiting examples, and from the appended Figures, wherein.

DETAILED DESCRIPTION OF THE INVENTION

Figure 1:
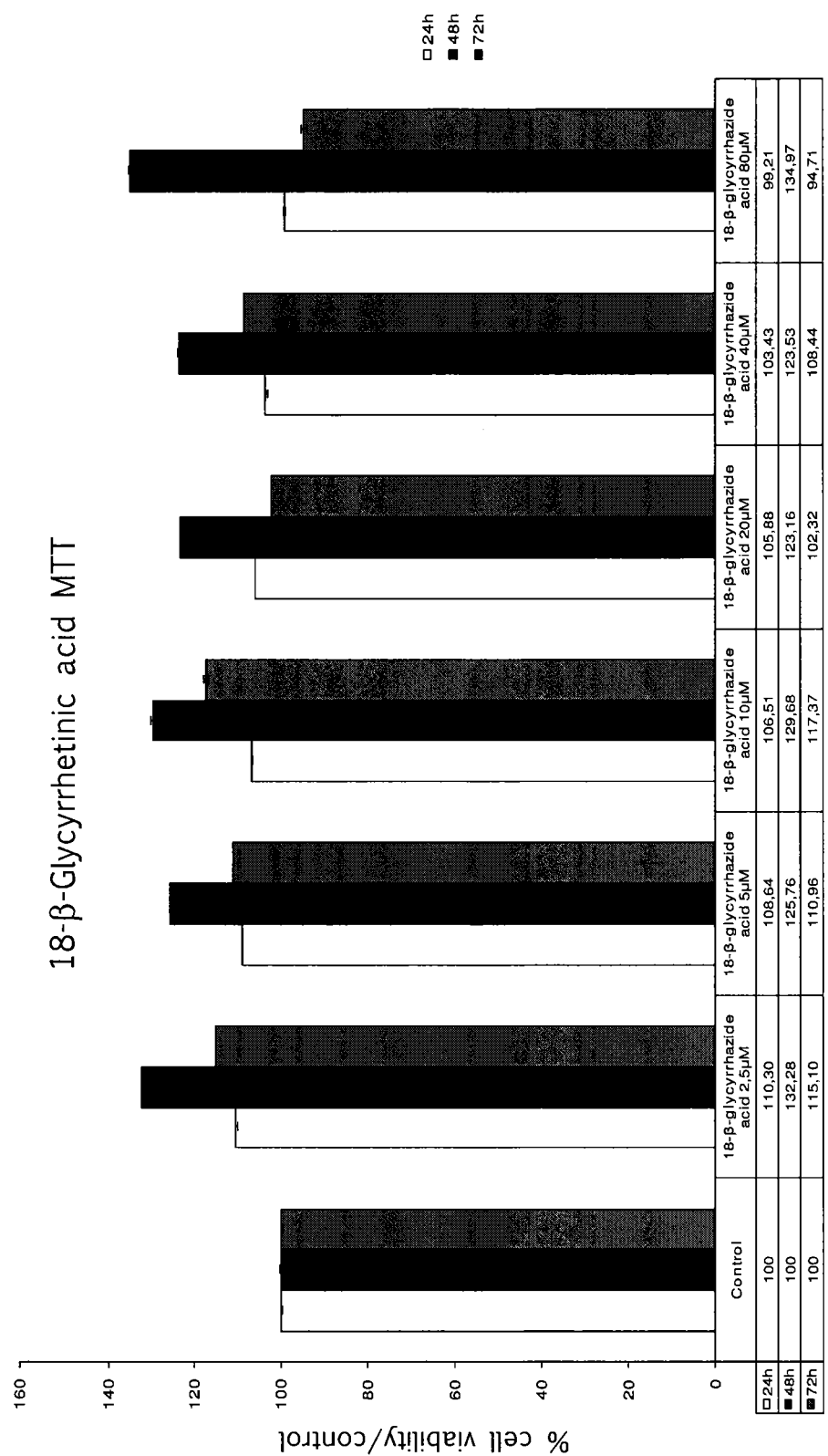
FIG. 1 shows the results of the MIT assay of 18-β-glycyrrhetinic acid (Example 5) after 24-48-72 hrs. of treatment: % viability as compared to control cells in human NCTC 2544 keratinocytes after 24-48-72 hrs. of treatment with 18-β-glycyrrhetinic acid at a concentration of 2.5-5-10-20-40-80 μM. The data represent mean values ±standard deviation. Each treatment was carried out in duplicate.

In particular, it was found that by esterifying with a sorbitol group [Sorb]$_n$ the carboxylic acid of the glycyrrhetinic acid moiety bound to the glycerol or polyglycerol (Polygly) molecule, the solubility of the resulting molecule is increased surprisingly.

The present invention therefore relates to an ester of the glycyrrhetinic acid having formula (I):

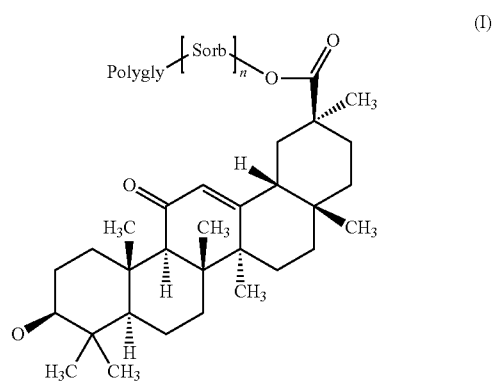

where n is an integer from 1 to 3,

Sorb represents at least one moiety of sorbitol, and

Polygly represents a moiety of glycerol or polyglycerol.

For the purposes of the present invention, the term polyglycerol means the products of condensation between molecules of glycerol, that is dimers, trimers, oligomers and polymers of glycerol. The simplest example is diglycerol or diglycerin which is obtained by condensing two molecules of glycerol. The dehydration reaction may involve all three hydroxyl groups of the molecule and therefore may have condensations of the alpha-alpha type (α-α, that is between two hydroxyls bound to primary carbon atoms of two molecules of glycerol), beta-beta (β-β, that is between two hydroxyls bound to secondary carbon atoms of two molecules of glycerol) and alpha-beta (α-β, that is between one hydroxyl bound to a primary carbon atom of a molecule of glycerol and one hydroxyl bound to a secondary carbon atom of another molecule of glycerol) type, as in the structures reported below:

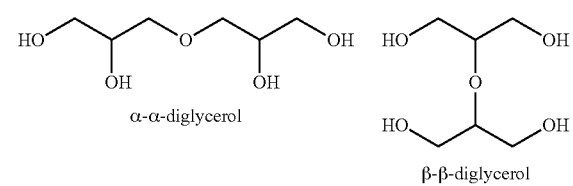

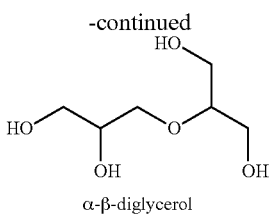

α-β-diglycerol

As the degree of polymerization increases also the number of potential isomers increases, for example it varies from three different linear isomers for diglycerol to eight different linear isomers for triglycerol.

Intramolecular reactions may also lead to the formation of cyclic products.

Typically, the processes currently available to obtain highly pure polyglycerols may be divided into two types:
- methods aimed at separating cyclic and secondary products, for example described in U.S. Pat. No. 3,968,169 the content of which is herein incorporated by reference in its entirety,
- methods to obtain highly pure linear products, for example described in U.S. Pat. No. 6,620,904 the content of which is herein incorporated by reference in its entirety.

For the purposes of the invention, the moieties of glycerol and oligomers thereof containing up to 10 units of monomer (polyglycerol-10) have been found to be particularly preferred; in fact, an increase in the degree of polymerization of polyglycerols corresponds to a decrease in their purity, together with the presence of an increasing number of moieties having a different molecular weight, which make the chemical-physical properties of the final polyesters less and less homogeneous. Furthermore, it should be noted that with an increase in the degree of polymerization, and thus in the molecular weight, an increase in the viscosity and a reduction of hygroscopy of the molecule are observed.

Typically, polyglycerols may be synthesized by resorting to methods providing for the condensation of glycerol with alkaline catalysis (dehydration thereof) with water elimination. The result of this synthesis normally is a mixture of oligomers which may comprise unreacted glycerol, cyclic products and very high oligomers. Conditions of temperature, typically above 200° C., synthesis duration and vacuum favour the formation of the desired structures. By dehydrating glycerin different polymers wherein the molecules of glycerin are bound to each other via an oxygen bridge are obtained. From glycerol containing three hydroxyl groups, the number of —OH increases by one per each condensing molecule of glycerin, therefore, diglycerol has four free —OH groups, triglycerol has five free —OH groups, tetraglycerol has six and so forth.

Preferably, in the ester of the invention, Polygly indicates a moiety of polyglycerol having a degree of polymerization from 1.5 to 10, more preferably indicates a moiety of polyglycerol having a degree of polymerization from 3 to 5.

According to some embodiments polyglycerol (polygly) having formula (I) contains 2 to 10 units of glycerol, preferably 2 or three units of (poly)glycerol.

In some embodiments of the invention, Polygly is a moiety of polyglycerol-3, more preferably the trimer wherein the three units of glycerol are bound to each other in a configuration α-α:

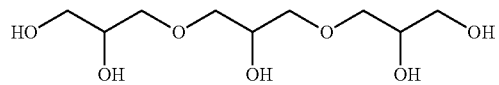

The moiety of sorbitol, that is Sorb, is present in the ester of the invention in a number from 1 to 3, preferably, the ester of the invention comprises only one moiety of sorbitol, n is 1.

According to a preferred embodiment, the ester of the present invention comprises a moiety of polyglycerol-3, wherein the three units of glycerol are bound to each other in a configuration α-α, and a moiety of sorbitol, having formula (Ia):

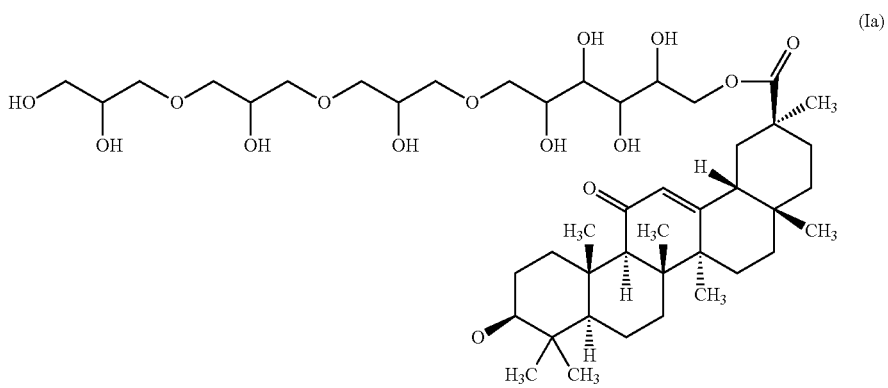

In other embodiments, the ester of the invention has the following formulae:

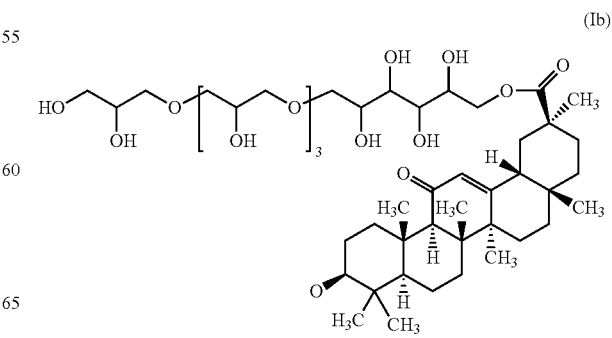

-continued

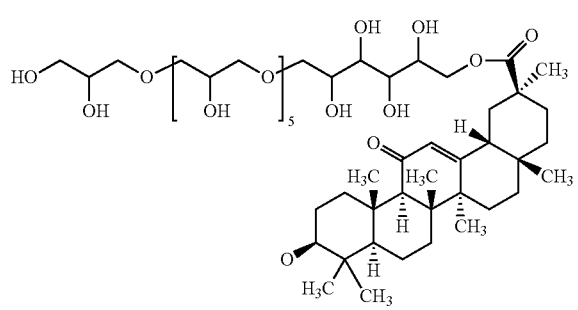
(Ic)

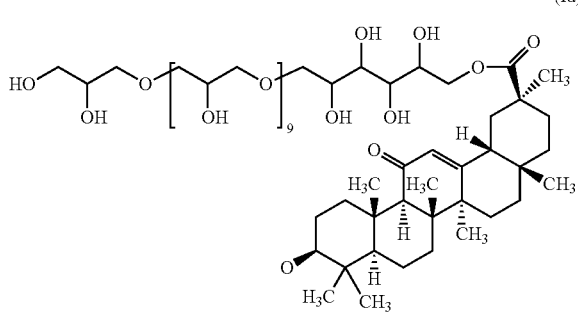
(Id)

According to another aspect, the present invention relates to a process for preparing the ester of glycyrrhetinic acid having formula (I), comprising the steps of:

i) reacting glycerol or polyglycerol with sorbitol to give an ether; and ii) reacting said ether with glycyrrhetinic acid to give the ester having formula (I).

In step i) glycerol or polyglycerol may be used pure or in a mixture thereof.

In some embodiments of the invention, glycerol or polyglycerol in a pure form are used.

Step ii) of esterification may be catalyzed by acids or bases. In some embodiments of the invention an acid catalyst is used, for example paratoluenesulfonic acid or methanesulfonic acid, or no added catalyst, in this case taking advantage of the acidity of glycyrrhetinic acid itself.

The laboratory synthesis may be carried out using different equipment. For example, a glass spherical reactor (flask) placed inside a microwave oven may be used, provided with an anchor mixer, a contact thermometer, a nitrogen suction pipe, a Claisen distiller complemented on top by a Graham distiller and in the last neck an addition funnel. Alternatively, it is possible to use a reactor consisting of a two-necked pyrex glass flask placed inside a laboratory electrical oven and connected to a three-necked glass candlestick, which allows the passage of the metal bar for mechanically stirring the product (central bar) and circulating a nitrogen flow. The reaction temperatures are variable and may be from 145° C. to 180° C. in case of a synthesis in a microwave oven, and from 130° C. to 220° C. in case of a synthesis in an electrical oven.

For the synthesis typically approximately equimolar amounts of glycerol or oligomers thereof and glycyrrhetinic acid are used or a slight excess of glycerol or polyglycerol is fed, for example 5-10%.

By conveniently adjusting the molar ratios between reagents and reaction times it is possible to obtain in the reaction product a prevalence of the desired ester.

According to a further aspect, the invention relates to an ester having formula (I) obtainable by the process of synthesis described above.

The characterization of the ester having formula (I) of the invention may be made through chromatographic means, in particular through the SEC technique (Size Exclusion Chromatography). With this technique, chromatograms are obtained that report peaks, corresponding to a substance or fraction exiting from the instrument, as a function of time; after having calibrated the instrument with reference compounds, conveniently having hydrodynamic volume similar to that of molecules or polymer to be detected; for example a polystyrene having a known molecular weight, the technique provides among others the values:

Mn, number average molecular weight (weights arithmetical average);
Mw, weight-average molecular weight (weighed average);
D (polydispersity), Mw/mn ratio.

The more the D value approaches 1, the more the molecule is pure.

The comparison between spectra $^1$H and $^{13}$C NMR (in $d_6$-DMSO) of glycyrrhetinic acid, of polyglycerol-3-sorbitol and of the reaction product or polyglycerol-3 sorbitol ester of glycyrrhetinic acid (formula I) according to an embodiment of the invention, show how in the product (ester) of the invention both signals of glycyrrhetinic acid, for example in the $^1$H-NMR the typical signals of 7 $CH_3$ groups at $\delta=0.5$-1.4 ppm and the signals of polyglycerol-3-sorbitol are present. On the other hand, the proton signal of the carboxyl group is absent to give evidence of the formation of ester linkage.

In the spectrum of the product the assessment of the integral of the proton signal present on the carbon-carbon double bond at $\delta=5.4$ ppm and its comparison with the integral of the polyglycerol-3-sorbitol protons at $\delta=3.1$-3.7 ppm determines the ratio between the two components comprised between about 1:3 and 1:4 (to the advantage of polyglycerol-3-sorbitol).

The presence of peaks at: 127 ppm relative to C $sp^2$ bound to C=O, at 170 ppm of C $sp^2$ without protons, at 178 ppm of the O—C=O group of the ester and at 200 ppm of C relative to carbonyl further confirm the formation of ester.

According to yet another aspect, the invention is related to cosmetic compositions, in particular compositions for topical use, comprising at least one ester of glycyrrhetinic acid having formula (I) and at least a cosmetically acceptable carrier. Cosmetically acceptable carriers suitable for the composition of the invention may be ingredients selected from rheology modifiers, plasticizers, emulsifiers, surfactants, wetting agents, refratting agents, solubilizing agents, colorants, lubricants, stabilizers, conditioning agents, fragrances, essential oils, adsorbents, preservatives, buffering agents, antimicrobial agents, antioxidants, antiseborrhoeic agents, antistatic agents, absorbent agents, chemical or physical solar filters, astringents, chelating agents, skin conditioning agents, covering agents, denaturant agents, depigmenting agents, emollients, emulsifying agents, non filmogenic agents, moisturising agents, hydrotrope agents, lenitive agents, smoothing agents, matting or pearly agents, skin protecting agents, reducing agents, refreshing agents, refatting agents, solvents, emulsions stabilizers, toning agents, wetting agents or mixtures thereof.

Compositions for topical use of the invention may be for rinsing or not and have properties suitable for applications in the cosmetic and dermatological field. According to some embodiments, at least one ester of glycyrrhetinic acid having formula (I) is present in the cosmetic composition of the invention in amounts from 0.01 to 20% by weight, preferably from 0.05 to 5% by weight on the composition weight.

The cosmetic composition of the invention may be in any forms suitable for local or topic application.

The composition of the invention may be in liquid form for example as a lotion, solution, suspension, shampoo, milk or in a solid or semi-solid or fluid form for example as a conditioner, serum, ointment or cream.

In some embodiments, the composition of the invention is in a liquid form for example in form of a water based lotion containing one or more carriers and/or excipients suitable for cosmetic applications.

In the liquid form, the composition may generally contain water from about 1 to 99.9% by weight. In some embodiments, water is present in amounts from 5 to 95% by weight. In other embodiments, water is present in amounts from 10 to 90% by weight.

In some embodiments of the invention, the cosmetic composition is anhydrous or it contains an amount of water less than 10% by weight.

In other embodiments of the invention, the cosmetically acceptable carrier is anhydrous or containing an amount of water less than 2% by weight, confined within a soft gelatin capsule.

In some embodiments, the carrier of the composition of the invention is a base preparation for cosmetic formulations, preferably for fluid preparations formulation suitable for skin application.

The composition of the invention may be applied, in a effective amount, directly onto the portion to be treated, typically face or body skin or on the scalp. In particularly preferred embodiments, the composition of the invention has the following formulations, where the concentration of each component is expressed in % by weight on the overall weight of the composition:

| Formulation 1 - MOISTURIZING SERUM | |
|---|---|
| Component | Concentration w/w (%) |
| Ammonium acryloyldimethyltaurate VP copolymer | 0.10-1.50 |
| Potassium sorbate | 0.01-0.10 |
| Sodium Benzoate | 0.01-0.10 |
| Pentylene glycol | 0.50-4.00 |
| Ester having formula (I) | 0.05-1.00 |
| Propanediol | 0.50-8.00 |
| Sodium hydroxide | 0.005-0.20 |
| Citric acid | q.s. at pH 5.2-5.4; |
| Glycerol | 0.50-8.00 |
| PEG-8 Dimethicone | 0.50-8.00 |
| Water | q.s. to 100 |

| Formulation 2 - LENITIVE SHAMPOO | |
|---|---|
| Component | Concentration w/w (%) |
| Disodium Laureth Sulphosuccinate | 1.00-7.00 |
| Di-PPG-2-Mireth-10 Adipate | 0.50-3.00 |
| Disodium Cocoamphodiacetate | 0.50-3.00 |
| Ammonium lauryl sulfate | 0.50-3.00 |
| Polyquaternium-10 | 0.10-0.50 |
| Tetrasodium EDTA | 0.05-0.20 |
| Fragrance | 0.10-1.50 |
| Hydrolysed cornstarch hydroxypropyltrimonium | 0.05-1.00 |
| BHA | 0.005-0.015 |
| Potassium chloride | 0.50-1.50 |
| Dimethicone PEG-7 isostearate | 0.5-1.50 |
| PEG-120 Methylglucose dioleate | 0.10-0.90 |
| Laureth-3 | 0.01-0.80 |
| PEG-90 Glyceryl Isostearate | 0.10-0.80 |
| PEG-8 Caprilic/Capric Glycerides | 0.50-1.00 |
| Ester having formula (I) | 0.05-1.00 |
| Sodium hydroxymethilglycinate | 0.20-0.45 |
| Citric acid | q.s. at pH 5.5-6.0 |
| Water | q.s. to 100 |

| Formulation 3 - MAKE-UP REMOVER | |
|---|---|
| Component | Concentration w/w (%) |
| Water | q.s. to 100 |
| Ethilhexylglycerin | 0.25-0.50 |
| PEG-40 Hydrogenated castor oil | 0.50-6.00 |
| PPG-26-Buteth-26 | 0.50-6.00 |
| Methylpropanediol | 0.50-4.00 |
| Propanediol | 0.10-6.00 |
| Disodium EDTA | 0.025-0.05 |
| Phenoxyethanol | 0.20-0.80 |
| Sodium hydroxide | q.s to pH 5.2 |
| Ester having formula (I) | 0.05-1.80 |

| Formulation 4 - BODY MILK | |
|---|---|
| Component | Concentration w/w (%) |
| Glycerine | 1.00-6.00 |
| Methylpropanediol | 1.00-6.00 |
| Cetyl Hydroxethylcellulose | 0.10-0.40 |
| Xanthan rubber | 0.10-0.40 |
| Tapioca starch | 1.00-2.00 |
| Disodium EDTA | 0.025-0.20 |
| Sorbitan Stearate | 2.00-5.00 |
| Sucrose cocoate | 0.10-1.00 |
| Ethylhexyl Palmitate | 1.00-5.00 |
| Hydrogenated polydecene | 100-5.00 |
| Caprilic/capric triglycerides | 1.00-5.00 |
| Sheabutter (*Butyrospermum parkii*) | 1.00-5.00 |
| Meadowfoam seed oil (*Limnanthes alba*) | 1.00-3.00 |
| Dimethicone | 1.00-3.00 |
| Sodium hydroxymethylglycinate | 0.10-0.20 |
| Ester having formula (I) | 0.05-1.00 |
| Phenoxyethanol | 0.70-0.90 |
| Lactic acid | q.s. at pH 5.5-6.0 |
| Fragrance | 0.30 |
| Delta tocopherol | 0.02-0.25 |
| Sorbitil furfural | 0.10-0.90 |
| Water | q.s. to 100 |

| Formulation 5 - TONING WATER | |
|---|---|
| Component | Concentration w/w (%) |
| Glycerin | 1.00-5.00 |
| Ester having formula (I) | 0.50-10.0 |
| Inositol | 0.05-0.50 |
| Trehalose | 0.50-1.00 |
| Allantoin | 0.001-0.10 |
| Fragrance | 0.05-0.30 |
| Phenoxyethanol | 0.3-0.60 |
| Sodium hydroxymethylglycinate | 0.05-0.20 |
| Lactic acid | q.s. at pH 5.5 ± 0.15 |
| PEG-40 Hydrogenated castor oil | 2.00-15.00 |
| Methylpropanediol | 1.00-6.00 |
| Ester having formula (I) | 0.05-1.50 |
| Water | q.s. to 100 |

According to another aspect of the invention, a method is provided for cosmetic treatment comprising the local application of an effective amount of a cosmetic application of the type described above.

The cosmetic compositions of the invention offer advantages compared to cosmetic or dermatological use of glycyrrhetinic acid as such or cosmetic compositions which contain it as will be apparent from the following Examples. Glycerol or polyglycerol are safe substances to be used and are able to form polymeric structures very different among them, linear, branched and iper-branched with better features of solubility and cytotoxicity compared to polyethilenic glycol polymers (used in known compositions). Moreover, by selecting a precise molecular weight of the polyglyceric chain, it is possible to modulate compositions properties that contain it, being these properties of the chemical physical type, for example solubility or absorption kinetics of the active ingredient, up to the realization of modified release forms of the glycyrrhetinic acid regulated by a chemical mechanism, due to the fact that the ester linkage, in certain conditions, can be susceptible towards hydrolysis or enzymatic cleavage in situ.

Applied onto the skin, the ester of the invention, due to the presence of a number of hydroxyl groups able to form hydrogen bridges with as many water molecules, behaves as a multifunction reservoir for glycyrrhetinic acid, able to normalize and moisture the skin in depth.

Finally, the ester of the invention is particularly advantageous, in the light of greater tolerability compared to glycyrrhetinic acid, in order to produce a sebum-normalizing action for the skin. As it is known, at the sebaceous glands level the androgen hormones concentration is the most important regulatory factor of the sebum secretion; in particular, the 5-alpha reductase enzyme converts 4-androstenedione into dihydrotestosterone, a metabolite able to significantly increase the sebaceous secretion.

A further advantage obtained with the cosmetic use of the ester of the invention is related to the antimicrobial action of glycyrrhetinic acid which produces an overall reduction of lipase activity of bacterial origin, associated to a lower production of free fat acids which determines a sebum-normalizing action towards skin.

It is understood that all the aspect identified as preferred and advantageous for the ester of the invention are also to be considered likewise preferred and advantageous for the cosmetic composition, the preparation process and the uses of the ester and the cosmetic composition.

Below are reported Examples of preparation of compounds according the present invention, as well as examples of assessment of their efficacy, provided by way of non-limiting examples.

In the experimental work referred to in the examples, the following starting materials have been used:
glycyrrhetinic acid, minimum 98% titer, Selectchemie, Milan-Italy;
polyglycerol-3, polyglycerol-4 and polyglycerol-6, CAS 25618-55-7: Pure Vegetable PG-3 Pure Vegetable PG-4 and Pure Vegetable PG-6, respectively Spiga Nord, Carasco (Genova), Italy;
polyglycerol-10, CAS 25618-55-7: Natrulon H10, Lonza;
sorbitol 70% Neosorb 70/70B not crystallizable Roquette Freres SA, (F);
sorbitol powder Neosorb P100 T Roquette Freres SA, (F).

Pure Vegetable PG-3 polyglycerol, preferred for the purposes of the invention, has been characterized with SEC test before its use, providing the following results: Mn=4818; Mw=4931; Mp=4693; D=1,023. The polydispersity index, equal to 1.02, indicates a very pure product, essentially formed only by a polyglycerol-3 unit.

As regards the polyglycerol purity, it has to be noted that commercial products used may also contain monomers and oligomers with lower and higher polymerization level. For example, Polyglycerol-3 may contain up to 15 of glycerol as well as polyglycerols with higher molecular weight.

EXAMPLES

Example 1

Preparation of Ester Having Formula (Ia)

i) Preparation of Polyglycerol-3 Ether and Sorbitol 240 g of polyglycerol-3 have been placed in a glass spherical reactor (flask) placed inside a microwave oven. The flask is provided with an anchor mixer, a contact thermometer, a nitrogen suction pipe, a Claisen distiller complemented on top by a Graham distiller and in the last neck an addition funnel.

After a first clearing with nitrogen, both heating and a slow stirring were activated. Once the temperature of 90/95° C. was reached, the system was placed under a very light stream of nitrogen.

0.25 g of methansolfonic acid were added, setting a vigorous stirring inside the reactor.

At this point, the reaction mixture was placed under high vacuum and 260 g of sorbitol (70% solution) dripped into the flask.

At the end of the addition of sorbitol (about 60 minutes), it was left to react for 2 hours more, always at a temperature of 90-95° C. Therefore, the reaction mixture was left to cool down.

ii) Preparation of Ester Having Formula (Ia)

404 g of polyglycerol-3 ether and sorbitol and 470 g of glycyrrhetinic acid have been placed in a glass spherical reactor (flask) placed inside a microwave oven. After a first clearing with nitrogen, heating was activated. Once the temperature of 120° C. was reached, the reaction mixture was placed under vacuum, the system was placed under light stirring and light stream of nitrogen. At 160° C., a vigorous stirring inside the reactor was set.

The distillation of reaction water started at about 146° C. During about 80 minutes, about 20% of the total reaction water was distilled. At this point, the course of esterification was followed by determining the acidity index (indicator: phenolphthalein).

When the acidity index reached a value lower than 5 and the temperature of 180° C. (generally after 60 minutes of reaction), the esterification was to be considered accomplished.

The system was cooled down at 80° C. and the reactor discharged.

The distillation of reaction water was significantly reduced when the product reached about 160° C. The duration of laboratory reaction was of about 3 hours. A dense product, slightly amber-coloured and nearly odourless was obtained.

Example 2

Preparation of Ester Having Formula (Ia)

i) Preparation of Polyglycerol-3 Ether and Sorbitol

If a conventional heating system is used, and not the microwave oven of the Example 1, the following variations have been considered:

After the clearing with nitrogen and slow stirring, the polyglycerol was heated at 120-140° C. and, once such a temperature was reached, the catalyst was added (methanesulfonic acid 0.20-0.35%).

Optionally, also 0.1% of hypophosphorous acid could be added in order to protect the product from excessive colouring.

Thereafter, the system was placed under vacuum at −0.5 bar relative to the atmospheric pressure.

182.17 g of powdered sorbitol were slowly added several times. The system was always kept at 140° C. under vacuum at 0.5 bar up to completion of the reaction (approximately 3-5 hours) and the obtaining of a highly clear viscous one phase even liquid product.

ii) Preparation of Ester Having Formula (Ia)

404 g of polyglycerol-3 ether and sorbitol and 470 g of glycyrrhetinic acid have been placed in a glass spherical reactor (flask).

After clearing with nitrogen and slow stirring, the reaction temperature was led to 150+10° C.

Once the desired temperature was reached, the catalyst was added, paratoluensulfonic acid, at a percentage equal to 0.3%.

If necessary, also 0.1% of hypophosphorous acid could be added in order to protect the product from excessive colouring.

The system was placed under vacuum at −0.5 bar (relative to the atmospheric pressure).

After about 3-4 hours, the reaction was completed, obtaining a highly viscous amber-coloured "one phase" even liquid product.

The course of esterification was followed by determining the acidity index that reached a value lower than 5 (indicator: phenolphthalein).

Example 3

Preparation of Ester Having Formula (Ib)

The process was as in Example 1, but in this case 314 g of polyglycerol-4 were used and thereafter (esterification with 18 beta glycyrrhetic acid) equimolar amounts of the two reagents.

Example 4

Preparation of Ester Having Formula (Ic)

The process was as in Example 1, but in this case 462 g of polyglycerol-6 were used and thereafter (esterification with 18 beta glycyrrhetic acid) equimolar amounts of the two reagents.

Example 5

Preparation of Ester Having Formula (Id)

The process was as in Example 1, but in this case 758 g of polyglycerol-10 were used and thereafter (esterification with 18 beta glycyrrhetic acid) equimolar amounts of the two reagents.

Example 6

Assessment of the Anti-Inflammatory Activity of the Ester Having Formula (Ia)

The anti-inflammatory effects of ester having formula (Ia) of Example 1 (referred to as 'POLY-GLY-S' for shortness of description) have been investigated in an in vitro inflammation model, on NCTC2544 human keratinocytes and using lipopolysaccharide (LPS) from *E. coli* as mediator of inflammatory state. The effect of derivative in the models used has been compared to that of 18-β-glycyrrhetic acid (referred to as '18-β' for shortness of description).

Furthermore, the in vitro inflammatory potential of POLY-GLY-S towards a positive control (cells treated with 5 μg/ml lipopolysaccharide) was determined. The data obtained have been compared to those obtained, in the same experimental model, using 18-β.

Materials

Biological Model

The NCTC2544 human keratinocytes line (Perry V. P. et Al., 1957) has been obtained from the Istituto Nazionale per la Ricerca sul Cancro, Genova, Italy.

Cell Line Culture and Propagation

The NCTC 2544 human keratinocytes immortalized line (Perry V. P. et al., 1957) kept in culture in sterile flasks (25 cm$^3$), incubated at 37° C. in wet atmosphere at 5% $CO_2$ in MEM culture medium (Minimum Essential Medium) supplemented with 10% fetal bovine serum (FBS), glutamine 2 mM, 1% non essential amino acids, in presence of 1% penicillin and streptomycin.

The 1:3 split is carried out every 2 days once the monolayer is reached, by washing with PBS 1× (phosphate buffer without $Ca^{2+}$ and $Mg^{2+}$) and by detaching cells with a solution of tripsin-EDTA at 37° C. for 2 minutes.

Reagents and Instruments Used

| REAGENTS | COMPANY |
| --- | --- |
| EMEM (EBSS) without L-glutamine | Lonza (BE12-125F) |
| Amino acids solution (100X) | Lonza (BE13-114E) |
| FBS ES | Lonza (DE14-850F) |
| PEN STREP MIX (Penicillin 10,000 UI/ml, Streptomicin 10,000 UI/ml) | Lonza (DE17-602F) |
| L-glutamine 200 mM | Lonza (BE17-605E) |
| DMSO | SIGMA (D1435) |
| PBS 1X w/o $Ca^{2+}$ or $Mg^{2+}$ | Lonza (BE17-516F) |
| Trypsin-versene mixture (EDTA) (1X) | Lonza (BE17-161E) |
| Trypan Blue | Sigma (T8154-20ML) |
| MEM Eagle EBSS (2X), W/O L-Gln, phenol red | Lonza (BE12-668-E) |
| MTT | Sigma (M2128 1G) |
| Chloroform | Sigma (366919) |
| Agarose | Sigma (A9539) |
| Etidium bromide solution | Sigma (E1510) |
| Gel Loading Buffer | Sigma (G2526) |
| Tri-Reagent | Sigma (T9424) |
| 2-Propanol | Sigma (59304) |
| Tris Acetate-EDTA buffer | Sigma (T9650) |
| Water | Sigma (95284) |
| High Capacity cDNA Reverse Transcription Kit | Applied Biosystems (4368814) |
| TaqMan ® Universal PCR Master Mix, No AmpErase ® UNG | Applied Biosystems (4324018) |
| Lipopolysaccharide from *E. Coli* | Sigma (L4391) |

| INSTRUMENTS | COMPANY |
| --- | --- |
| Inverted phase/contrast microscope | Leica |
| Laminar flow hood | Steril Manifacturing Division |
| HeraCell CO2 (Mod: 150 ADV) incubator | Thermo Scientific |
| Thermostated digital bath | Stuart |
| Horizontal freezer −80° C. | Elcold |
| Burker chamber | Carlo Erba |
| Scale (Mod. AM100) | Mettler |

-continued

| INSTRUMENTS | COMPANY |
|---|---|
| Spectrophotometric microplate reader (Mod: ELX808) + Gen5 Software | BioTek |
| UV-visible spectrophotometer (MOD: 6715, BS-6715B0) | JenWay |
| Analog vortex (Mod. Sa8, BS-SAB) | Stuart |
| Real time PCR system (Mod: Mx3000P) | Stratagene |
| PcDell + Software MX3000P version 1.2 and 2.00 | Stratagene |
| Trans-UV (ACDM-ECXF15M) | Vilber Lourmat |
| Horizontal electrophoresis chamber (MOD: 250-5159) | Ward |
| Electrophoresis chamber power supply (MOD: 36-5112) | Ward |
| Digital camera + UV protection device (S630) | Samsung |
| Benchtop centrifuge (Galaxy 7d) | VWR |
| Mixer (TR13) | Girmy |

Tested Active Compounds

| NAME | 'POLY-GLY-S' | '18-β' |
|---|---|---|
| UNIQUE IDENTIFYING NAME | Ester having formula (Ia) (Example 1) | 18-beta-glycyrrhetic acid |
| STORAGE | rt | rt |
| CONCENTRATIONS | 0.625, 1.25, 2, 2.5, 5, 10, 20, 25, 40, 50, 80 μM* | 2.5, 5, 10, 20, 25, 40, 50, 80 μM* |

*All the concentrations refer to the active compound in the usage matrix

Control

Negative Control: NCTC2544 human keratinocytes kept in culture in EMEM (EBSS) at 2.5% FBS, supplemented with L-glutamine 2 mM, 1% amino acid solution and 1% penicillin (10,000 U/ml)/streptomycin (10,000 Ug/ml) mixture at 37° C., 5% $CO_2$.

Positive Control: NCTC2544 human keratinocytes treated with LPS (5 μg/ml) in EMEM (EBSS) at 2.5% FBS, supplemented with L-glutamine 2 mM, 1% amino acid solution and 1% penicillin (10,000 U/ml)/streptomycin (10,000 Ug/ml) mixture at 37° C., 5% $CO_2$.

Methods

MTT Assay

The MTT test is useful to assess in vitro cell viability following the treatment with diluted compounds. The MTT method has been used as an indirect measure of cell viability.

The effects on NCTC 2544 cell proliferation from compounds 18-β and POLY-GLY-S at different concentrations have been examined.

Figure 2:
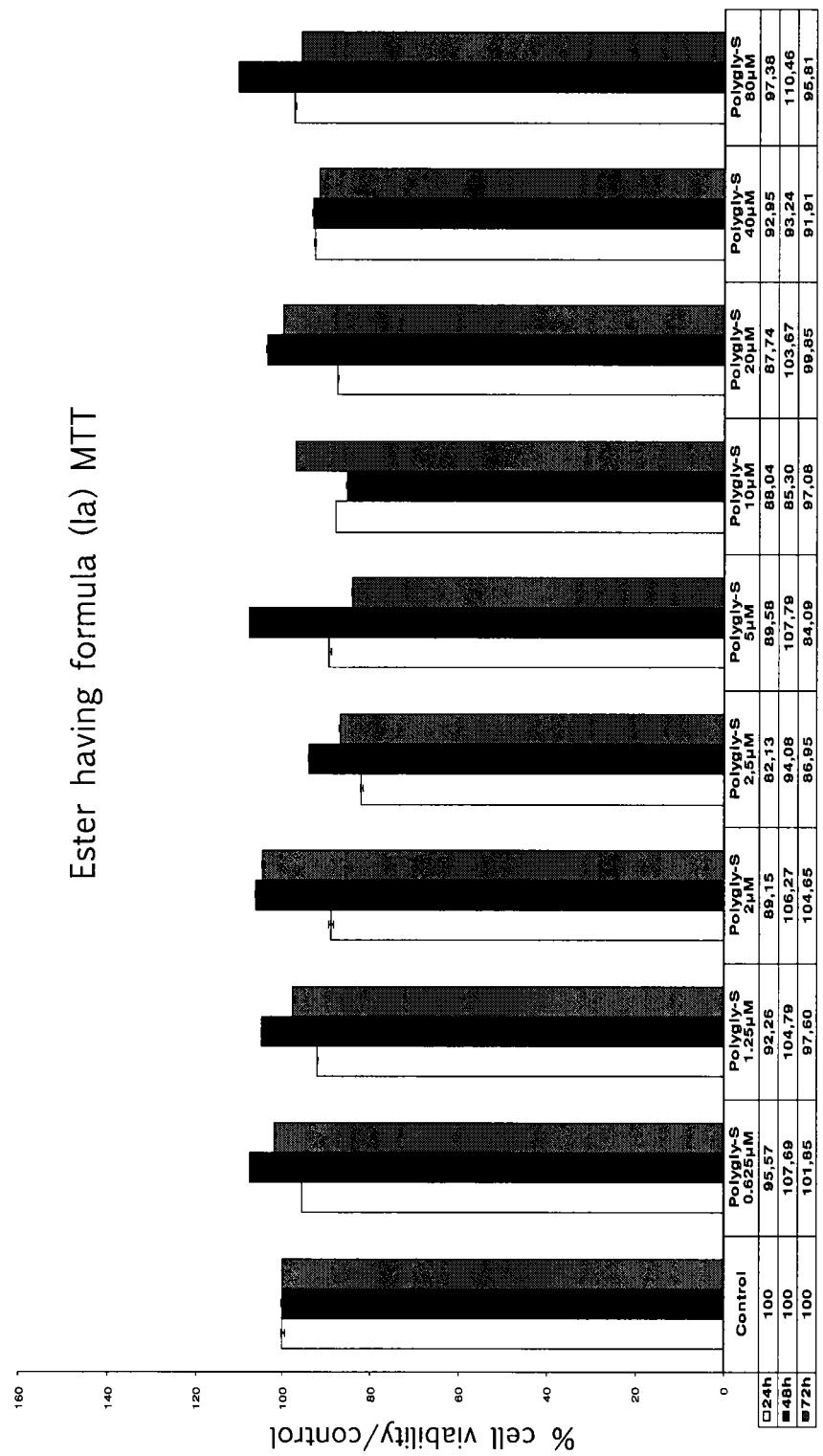
FIG. 2 shows the results of the MTT assay of the ester having formula (Ia) (Example 5) after 24-48-72 hrs. of treatment: % viability in human NCTC 2544 keratinocytes after 24-48-72 hrs. of treatment with the ester having formula (Ia) at a concentration of 0.625-1.25-2-2.5-5-10-20-40-80 μM. The data are expressed as mean values ±standard deviation. Each treatment was carried out in duplicate.

The cells have been plated at low densities and treated with different concentrations of active compounds and negative control, in culture medium EMEM, without phenol red supplemented at 10% with FCS, 2 mM L-glutamine, 1% NEAA solution and 1% antibiotic mixture for 24, 48 and 72 hours and cell viability has been assessed by the MTT assay. The cell viability percentage compared to control (FIGS. 1-2) has been calculated after 24, 48 and 72 hours of incubation. The test showed that after 24 hours of incubation, none of the 18-β-glycyrrhetic acid (FIG. 1) and of ester having formula (Ia) (FIG. 2) concentrations showed a cytotoxic effect on NCTC2544 compared to control. The same results have been obtained after a prolonged cells exposure (48-72 hours) to tested compounds for all the considered concentrations.

Inflammation Assessment Assay

The expression of the TNF-α gene on NCTC 2544 cells was assessed by RT-PCR.

The gene expression analysis implies four steps:
1. Cell treatment with active compounds for 48 hrs;
2. RNA extraction;
3. cDNA reverse transcription;
4. quantitative reverse transcription.

NCTC2544 Cells Treatment

In experimental conditions, in connection with the results obtained in the previous MIT assay, POLY-GLY-S and 18-β have been tested at a concentration of 20 μM (final concentration in the culture medium). Both positive control and negative control have been tested.

Anti-Inflammatory Test on NCTC2544

Day 1: Cell Seeding

When the cells (NCTC 2544 human keratinocytes) had reached about 80% confluence, they were removed with trypsin/EDTA and seeded at a density of $1\times10^6$ cells/ml in 12-well plates and then incubated at 37° C., 5% $CO_2$ (24 h).

Days 2-3: Exposure to Substances for 48 Hours

When the cells had reached about 80% confluence, the complete medium was removed; cells were washed with PBS 1× and incubated in EMEN (EBSS) with 2.5% FBS, supplemented with 2 mM L-glutamine, 1% NEAA solution and 1% antibiotic mixture at 37° C., 5% $CO_2$ for at least 4 hrs.

POLY-GLY-S and 18-β were dissolved in EMEN supplemented with 2.5% FBS, 2 mM L-glutamine, 1% NEAA solution and 1% penicillin (10,000 U/ml)/streptomycin (10,000 μg/ml) mixture.

Controls only containing culture medium (negative control) and culture medium plus LPS (5 μg/ml) (positive control) have been included in each plate.

Cells were exposed to increasing concentrations of compounds to be tested, i.e. 2.5-5-10 μM.

To each well LPS at a concentration of 5 μg/ml was added. Each sample was tested in duplicate.

Then cells were incubated at 37° C., 5% $CO_2$ for 24 hrs.

RNA Extraction

Total RNA was extracted from cells using a single homogeneous solution Tri-reagent (Sigma Aldrich) to isolate RNA following manufacturer's instructions.

The purity of the extracted total RNA was assessed reading the absorbance at 260 nm, i.e. λ value corresponding to the maximum absorbance of the nucleic acid. The absorbance at 280 nm was also read in order to assess the protein or phenol contamination. RNA was considered to be of good quality if R=A260/A280 ratio was >1.4.

After determining the total RNA concentration and the purity each RNA sample was diluted in DEPC water at a final concentration of 2 μg/ml. This is the concentration required by the reverse transcription kit. An electrophoresis run on gel was also carried out in order to assess the extracted total RNA integrity.

Reverse Transcription in cDNA

The extracted and quantified total RNA was amplified using the "High-Capacity cDNA Reverse transcription Kit" (Applied Biosystems).

Random primer were used in order to ensure an effective synthesis of the mRNA first strand.

RT-PCR System Mx3000P (Stratagene) was used for amplification and each total RNA was amplified in duplicate.

| Amplification Conditions | Step 1: | Step 2: | Step 3: | Step 4: |
|---|---|---|---|---|
| Temperature | 25° C. | 37° C. | 85° C. | 25° C. |
| Time | 10 mins | 120 mins | 60 sec | hold |

After amplification, samples were diluted with 30 μl of DEPC water and stored at −20° C. until use.

Real Time PCR

RT-PCR was carried out using TaqMan linear probes (Applied Biosystems). These probes are the most used and published detection system for qPCR applications. In stock probes and primer were selected based on previous specific bibliographic studies.

The relative quantification method was used where the gene relative concentration of interest (target) is compared with unknown samples to a calibrator or control sample (untreated cells).

The following genes were used:

| GENE NAME | TAQMAN ASSAY ID | Amplification Program | Amplicon length |
|---|---|---|---|
| GAPDH (housekeeping) | Hs99999905_m1 | 95° C. 15 s 60° C. 60 s for 40 cycles | 122 |
| TNF-α (target) | Hs00174128_m1 | 95° C. 15 s 60° C. 60 s for 40 cycles | 105 |

Experimental Procedure

RT-PCR was carried out using cell treated at different times of treatment and control cells cDNAs.

10 μl TaqMan 2× Gene Expression master Mix and 1 μl 20× TaqMan Gene Expression were added to cDNA. Each biological sample was treated in duplicate and amplified as indicated in the table:

| | STEP | | | |
|---|---|---|---|---|
| | Step 1: UDG | Step 2: Activation of AmpliTaq Gold | Step 3: PCR Cycle (50 cycles) | |
| | incubation Hold | DNA Polymerase Hold | Denature | Anneal/ Extend |
| Temperature | 50° C. | 95° C. | 95° C. | 60° C. |
| Time | 2 mins | 10 mins | 15 sec | Hold |

Collection of Data

The data provided from Stratagene Mx3000P instrument have been registered from the internal software MXpro v.4.01. Once the amplification was complete, the software automatically applies the $2^{-\Delta\Delta Ct}$ method. Target and normalizer Ct values should ideally be within about ten cycles from each other.

The resulting comparative quantification is a relative comparative diagram. A value equal to one means no changes in the gene expression of the target gene between the sample being studied and the calibrator, whereas if it is higher it means up-regulation, if lower than one it means down-regulation. A value is significantly regarded as significant if it is higher or lower than once (up-regulated or down-regulated) compared to the calibrator.

Results

TNF-α is typically over expressed in the skin of individuals suffering from psoriasis (Kristensen et al, 1993; Ettehadi et al, 1994) and plays a major role in the pathogenesis of the disease. TNF-α key role is further supported by both the evidence that in psoriasis other genes regulated by TNF-α are over expressed and that TNF-α antagonists are used as highly effective therapeutic agents in most of the patients (Richardson e Gelfand, 2008). Recently, it has been suggested that TNF-α inhibits barrier proteins expression (for example FLG and LOR), that TNF-α antagonists may contribute to clinical improvement of patients suffering from psoriasis increasing barrier proteins expression (Kim et al., 2011).

McRitchie et al. (1997) have recently showed that 10 μg/ml LPS from E. coli massively stimulates the TNF-α production by alveolar epithelial cells within 4 hrs. In the undertaken study, it was found that the treatment with LPS from E. coli (5 μg/ml) had a similar effect on TNF-α induction and therefore of the inflammatory process on NCTC 2544 cells starting from 16 hrs of treatment.

In fact, it was assessed that the NCTC2544 treatment for 16, 24 and 48 hours with LPS (5 μg/ml) in low FBS EMEM (2.5%) significantly stimulated the TNF-α production and therefore the expression of the TNF-α gene on NCTC 2544 cells after exposure to the two compounds being examined was studied.

Figure 3:
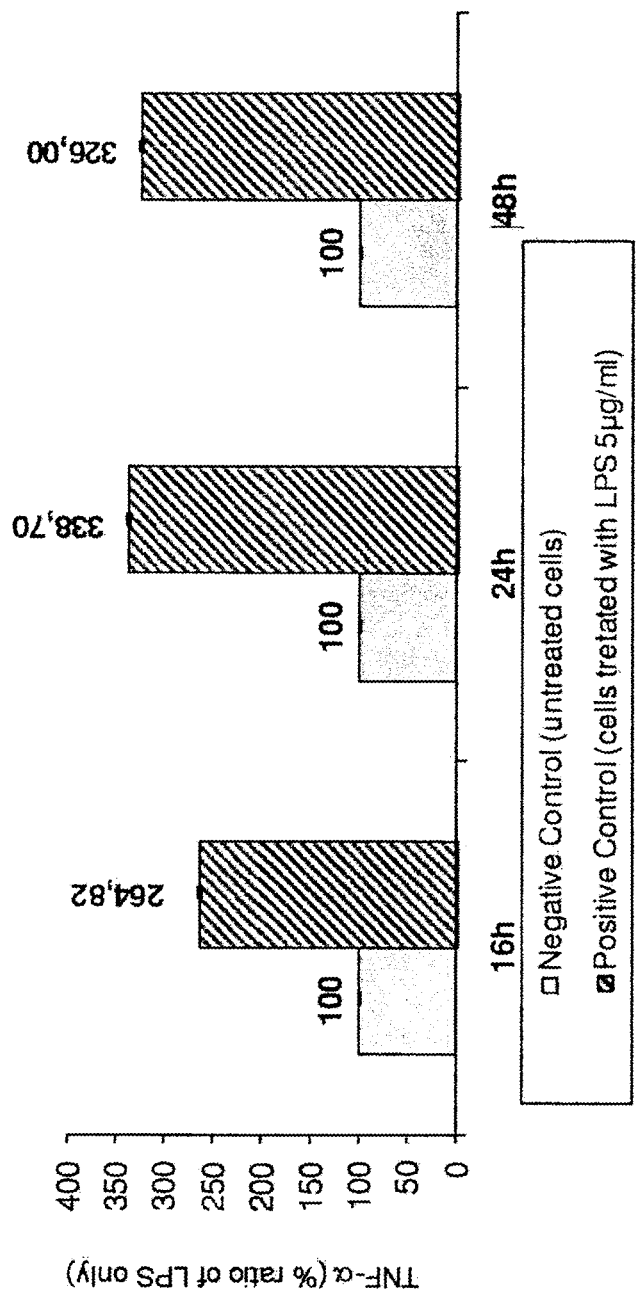
FIG. 3 shows the expression of the gene of tumour necrosis factor alpha (TNF-α) in human NCTC 2544 keratinocytes as determined by RT-PCR in Example 6. The NCTC 2544 cells were treated at 37° C. for 16, 24 and 48 hours, at 5% $CO_2$, with: basal culture medium, containing 2.5% fetal bovine serum (negative control) and with: basal culture medium, containing 2.5% fetal bovine serum supplemented with LPS (5 μg/ml) (positive control). The values represent the mean values of 2 experiments in duplicate.

At 16 hrs of incubation, a significant difference (P<0.05) between the expression of the TNF-α gene compared to the negative control and the NCTC 2544 cells treated with LPS (5 μg/ml) (negative control) was found (FIG. 3). Compared to the negative control, the expression of the TNF-α gene in NCTC 2544 cells significantly increased (P<0.05) of about three times after 24 hours of treatment with LPS (5 μg/ml) and this effect was kept also after 48 hrs of incubation (FIG. 3).

Figure 4:
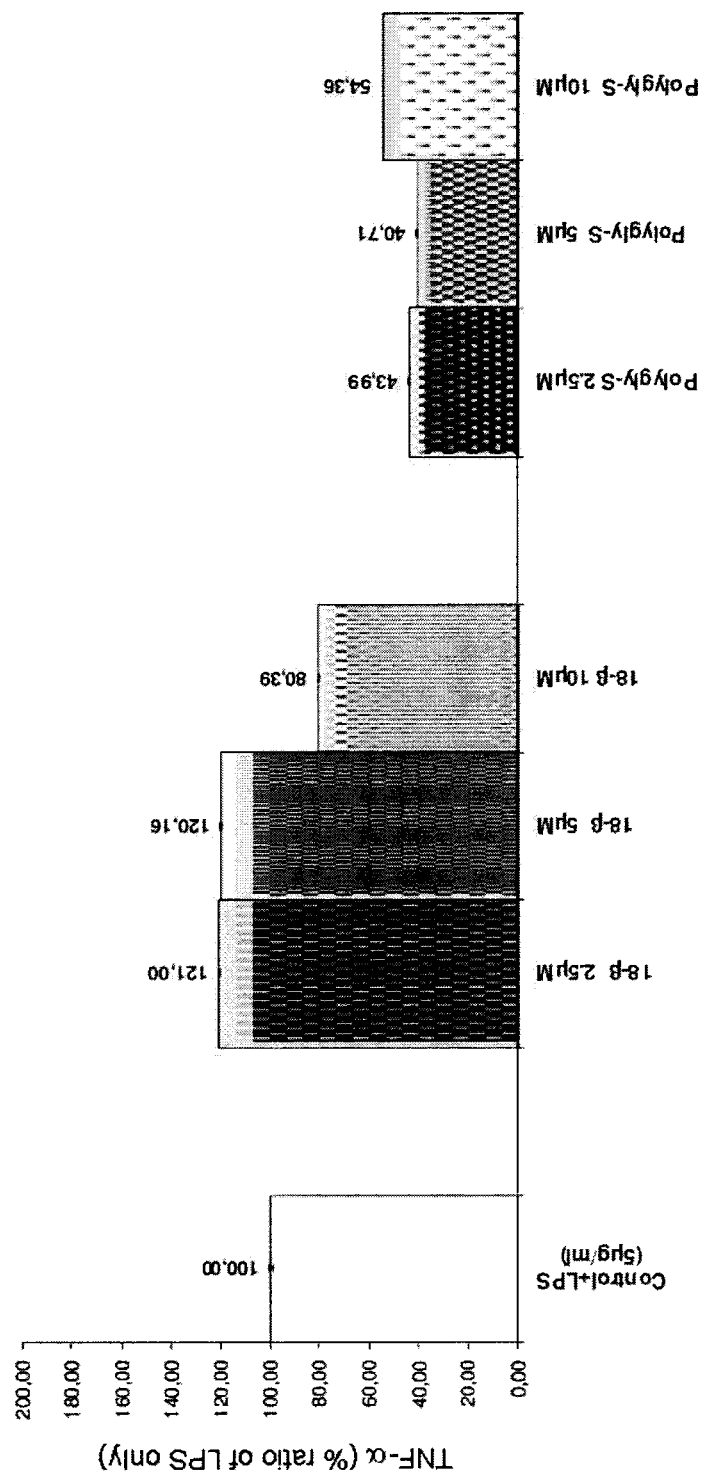
FIG. 4 shows the expression of the gene of tumour necrosis factor alpha (TNF-α) in human NCTC 2544 keratinocytes as determined by RT-PCR in Example 6. The NCTC 2544 cells were treated at 37° C. for 48 hours, at 5% $CO_2$, with: basal culture medium, containing 2.5% fetal bovine serum (negative control), with: basal culture medium, containing 2.5% fetal bovine serum supplemented with LPS (5 μg/ml) (positive control), with: basal culture medium, containing 2.5% fetal bovine serum supplemented with LPS (5 μg/ml) and 18-β-glycyrrhetinic acid (18-β) at a concentration of 2.5-5-10 μM, with: basal culture medium, containing 2.5% fetal bovine serum supplemented with LPS (5 μg/ml), and POLYGLY-S at a concentration of 2.5-5-10 μM. The results are expressed as a percentage of inflammation as compared to cells treated with LPS. The values represent the mean values of 2 experiments in duplicate.
Figure 5:
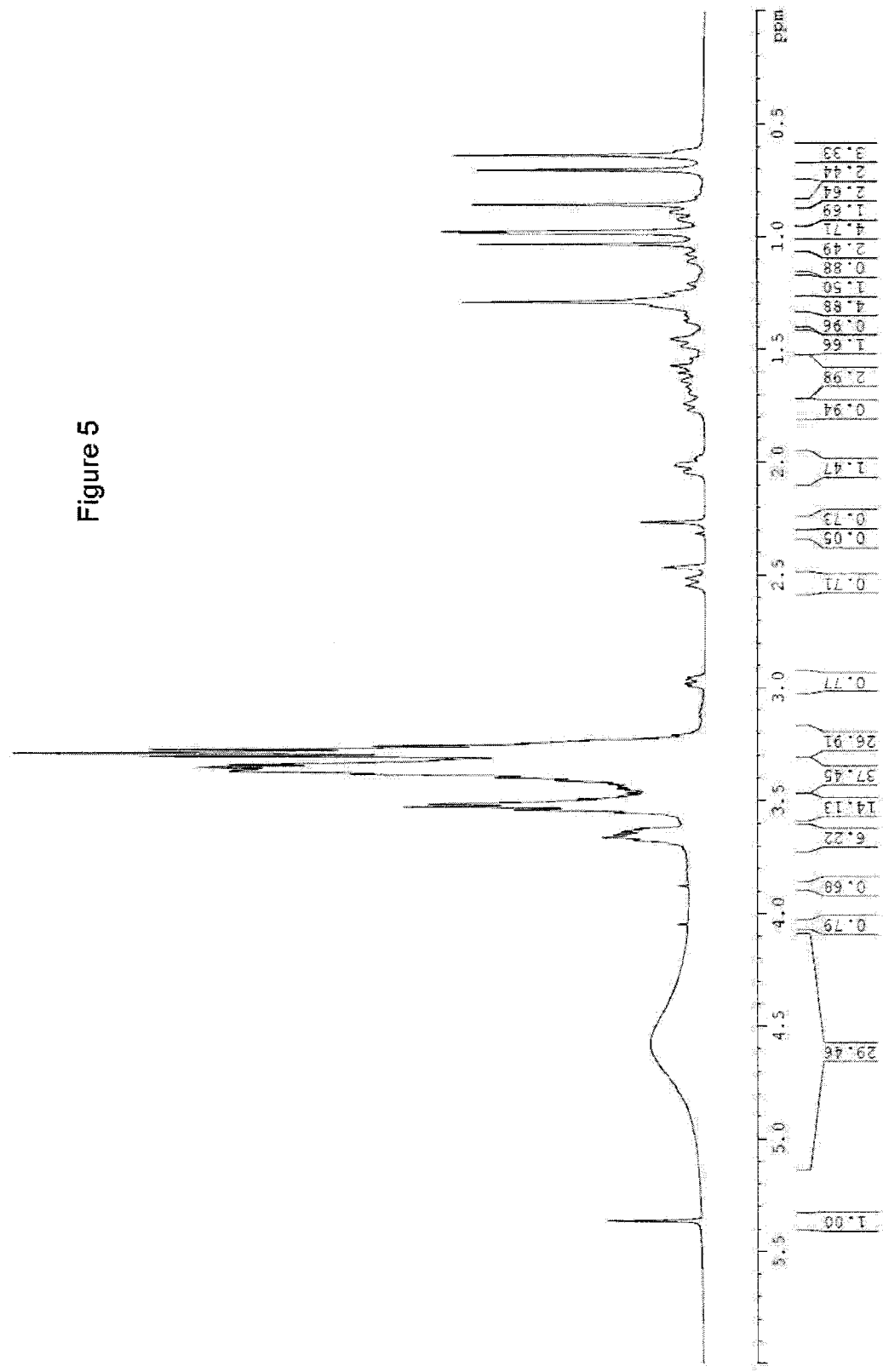
FIG. 5 shows the $^1$H NMR spectrum (in $d_6$-DMSO) of the glycyrrhetinic ester of polyglycerol-3-sorbitol, according to an embodiment of formula (I)
Figure 6:
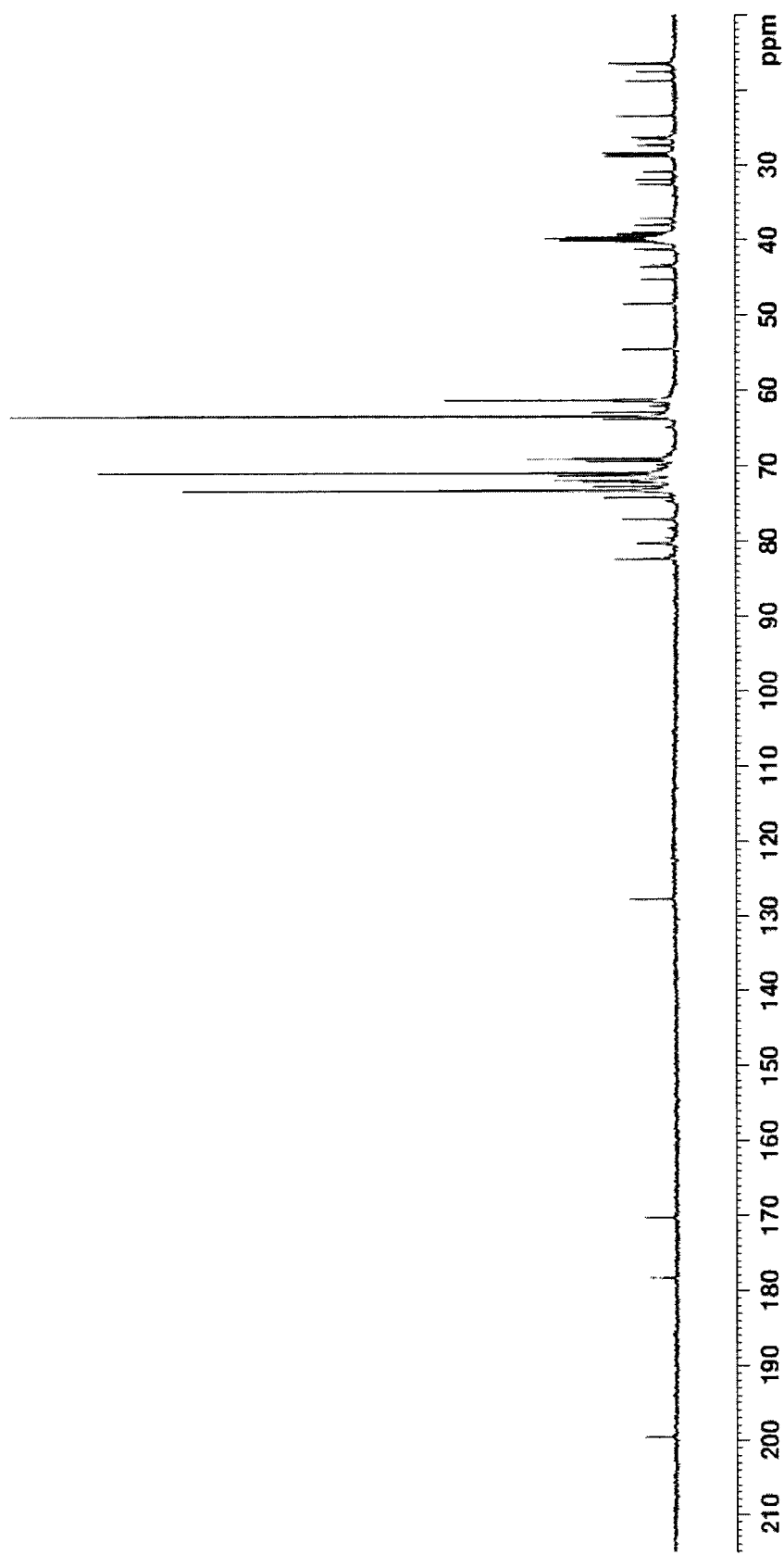
FIG. 6 shows the $^{13}$C NMR spectrum (in $d_6$-DMSO) of the glycyrrhetinic ester of polyglycerol-3-sorbitol, according to an embodiment of formula (I)
Figure 7:
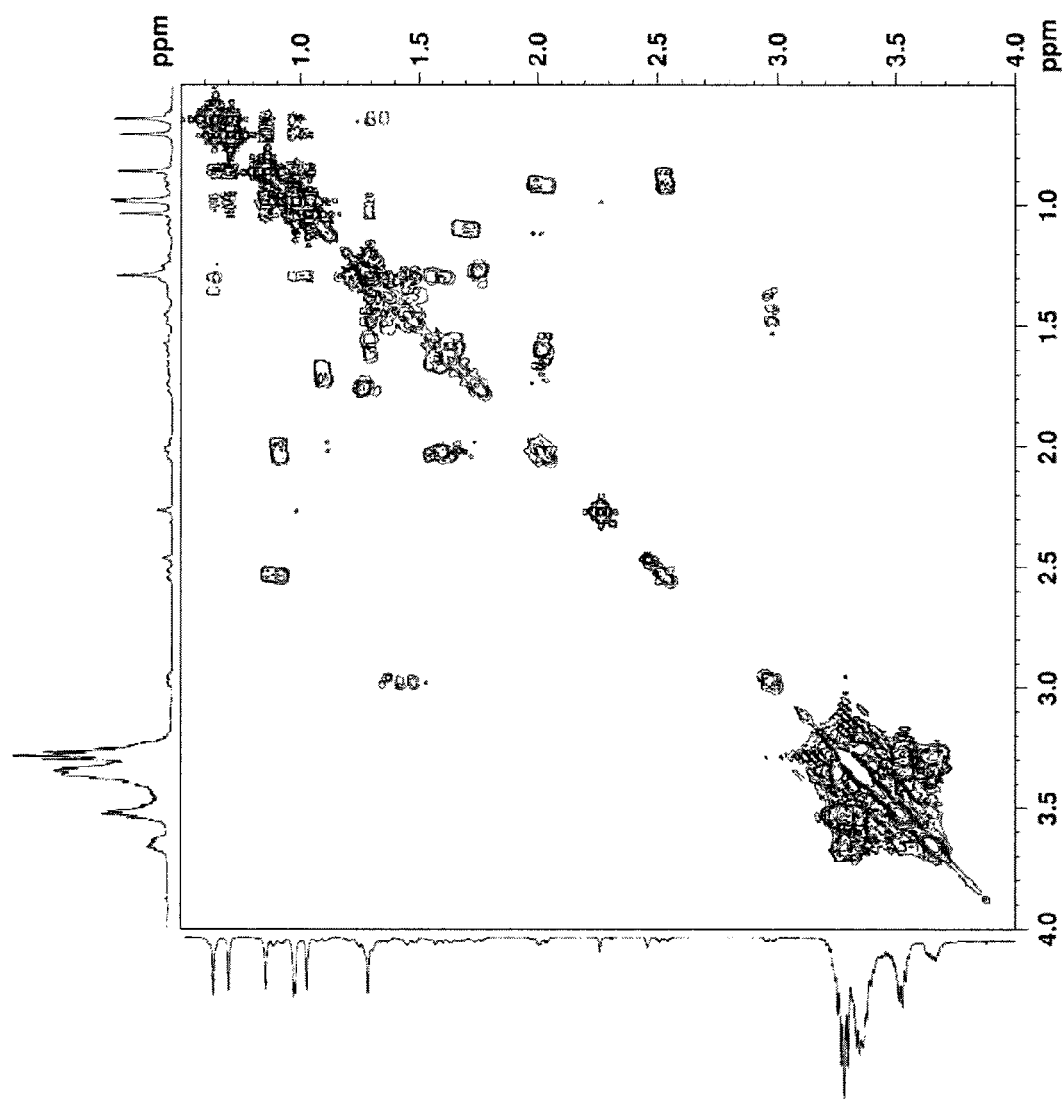
FIG. 7 shows the 2-dimensional spectrum COSY$^1$H NMR (in $d_6$-DMSO) of the glycyrrhetinic ester of polyglycerol-3-sorbitol, according to an embodiment of formula (I)

After this experiment of preliminary validation, the expression of the TNF-α gene was assessed by RT-PCR on NCTC 2544 cells, after treatments with 2.5-5 and 10 μm 18-β, and 2.5-5 and 10 μm POLY-GLY-S, added on cells with LPS at 5 μg/ml in low FBS EMEM (2.5%). For a better representation of collected data, the results have been expressed as percentage ratio compared to cells treated only with LPS. After 48 hrs of treatment (FIG. 4), 18-β no longer had anti-inflammatory effect. On the contrary, POLY-GLY-S (FIG. 4) at all concentrations assayed was significantly effective (P<0.05) at inhibiting the expression of the TNF-α gene. On the other hand, inhibition percentages of the expression of the TNF-α gene were higher than the same concentrations of 18-β. In particular, 2.5, 5 and 10 μM POLY-GLY-S produced an inhibition of 43.99%, 40.71% and 54.36%, respectively.

CONCLUSIONS

Based on the obtained data, it is noted that, when used at 2.5-5 and 10 μM, both 8-β and POLY-GLY-S were well tolerated by NCTC2544 human keratinocytes. As regards the anti-inflammatory assay, the validation of the method used was first assessed since it was noted a clear increase of TNF-α after cell treatment with LPS 5 μg/ml compared with untreated cells.

POLY-GLY-S showed an anti-inflammatory effect on the expression of the TNF-α gene after 48 hours of incubation. At all the concentrations assayed, POLY-GLY-S was able to reduce the expression of the TNF-α gene of at least 50% producing an inhibitory effect higher than that produced by 18-β.

The invention claimed is:

1. An ester of glycyrrhetinic acid having formula (I):

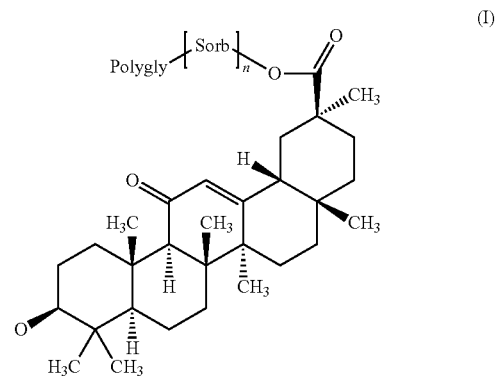

wherein
n is an integer from 1 to 3,
Sorb represents a moiety of sorbitol, and
Polygly represents a moiety of glycerol or polyglycerol.

2. The ester of claim 1, wherein Polygly represents a moiety of polyglycerol having a polymerization degree of 1.5 to 10.

3. The ester of claim 2, wherein Polygly represents a moiety of polyglycerol having a polymerization degree of 3 to 5.

4. The ester of claim 1, wherein n is 1.

5. The ester of claim 1 having formula (Ia):

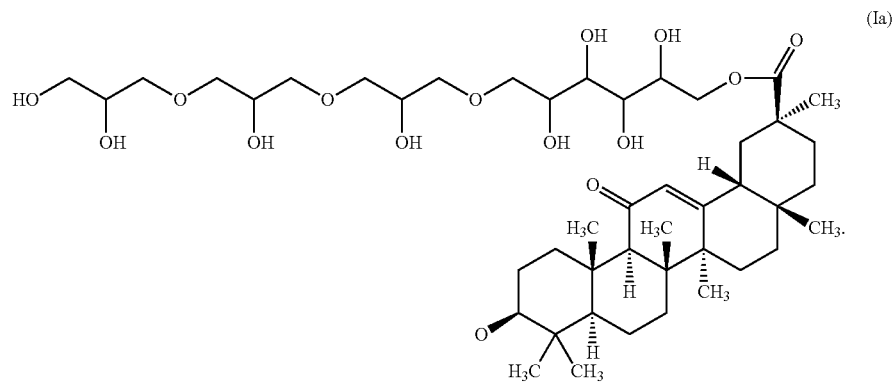

6. A cosmetic composition comprising at least one ester of claim 1 and at least one cosmetically acceptable carrier.

7. A cosmetic anti-ageing method of treatment of skin comprising the application to the skin of an effective anti-ageing amount of an ester of glycyrrhetinic acid having formula (I) according to claim 1.

8. A cosmetic lenitive method of treatment of skin comprising the application to the skin of an effective lenitive amount of a glycyrrhetinic acid having formula (I) according to claim 1.

9. A cosmetic method of treatment of skin comprising the application to the skin of a cosmetically effective amount of a cosmetic composition of claim 6.

10. A process for preparing the ester of glycyrrhetinic acid having formula (I), according to claim 1, comprising the steps of:
   i) reacting glycerol or polyglycerol with sorbitol to give an ether; and
   ii) reacting said ether with glycyrrhetinic acid to give the ester having formula (I).

* * * * *